United States Patent [19]

Bene

[11] Patent Number: 4,988,485
[45] Date of Patent: Jan. 29, 1991

[54] DEVICE FOR CLEANING AND DISINFECTING MEDICAL AND SURGICAL INSTRUMENTS

[76] Inventor: Pierre-Yves Bene, 47, Boulevard des Belges, 69006 Lyon, France

[21] Appl. No.: 468,098

[22] Filed: Jan. 23, 1990

[30] Foreign Application Priority Data

Jan. 20, 1989 [FR] France ............................ 89 01306

[51] Int. Cl.⁵ ............................................... A61L 2/16
[52] U.S. Cl. ........................................ 422/292; 422/28; 422/300; 34/90; 34/202; 134/100; 134/102; 134/199; 239/419; 239/430; 239/558; 239/590.3; 239/590.5
[58] Field of Search ............... 422/1, 28, 30, 33, 292, 422/300, 297; 134/100, 102, 199; 34/90, 202; 239/398, 419, 430, 558, 590.3, 590.5

[56] References Cited

U.S. PATENT DOCUMENTS

| | | | |
|---|---|---|---|
| 3,699,984 | 10/1972 | Davis | 134/199 |
| 3,918,987 | 11/1975 | Kopfer | 134/199 |
| 4,064,886 | 12/1977 | Hechele | 134/95 |
| 4,160,457 | 7/1979 | Dickson, Jr. et al. | 134/199 |
| 4,552,163 | 11/1985 | Biancalana | 422/292 |
| 4,817,651 | 4/1989 | Crisp et al. | 134/199 |

FOREIGN PATENT DOCUMENTS 0056791 7/1982 European Pat. Off. .
0287481 10/1988 European Pat. Off. .

Primary Examiner—Robert J. Warden
Assistant Examiner—Lynn M. Kummert
Attorney, Agent, or Firm—Oliff & Berridge

[57] ABSTRACT

This device comprises a tubular body (2) into which open discharge nozzles (5) for an atomized product constituted by disinfection liquid and pressurized air.

The air supply means of the injectors comprise an annular duct (14) extending through 360° and directly supplying the injectors (6), while the liquid supply means of the injectors comprise several stages (15,17) with the fluid vein separated in two at each stage.

14 Claims, 2 Drawing Sheets

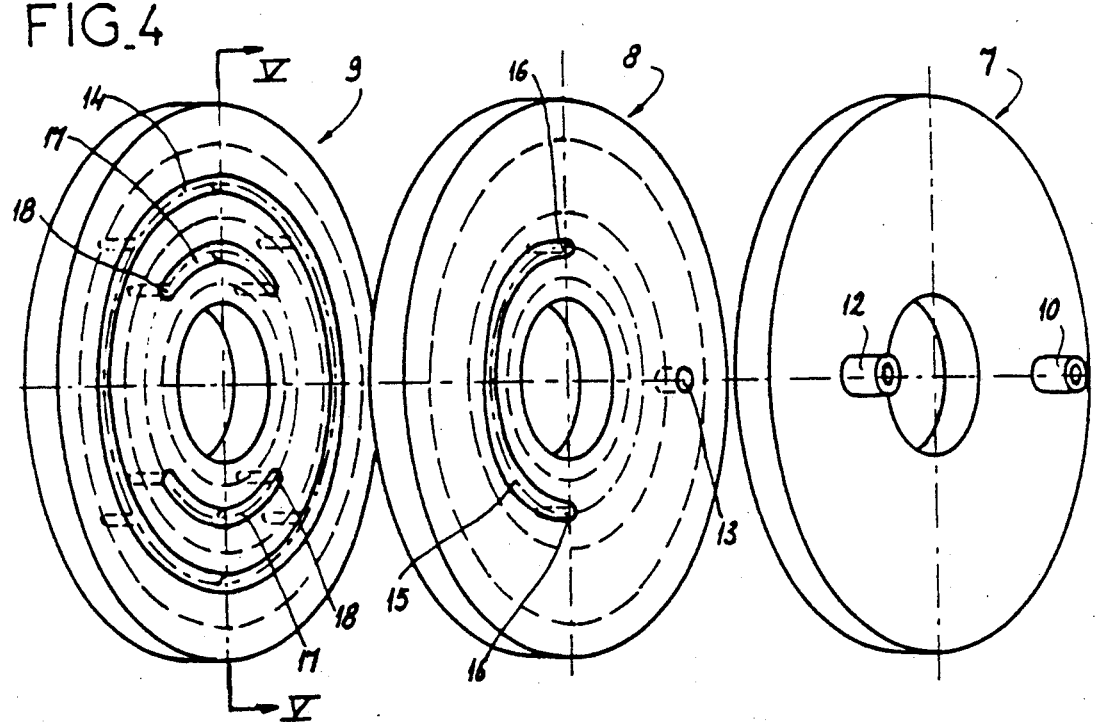
FIG.4
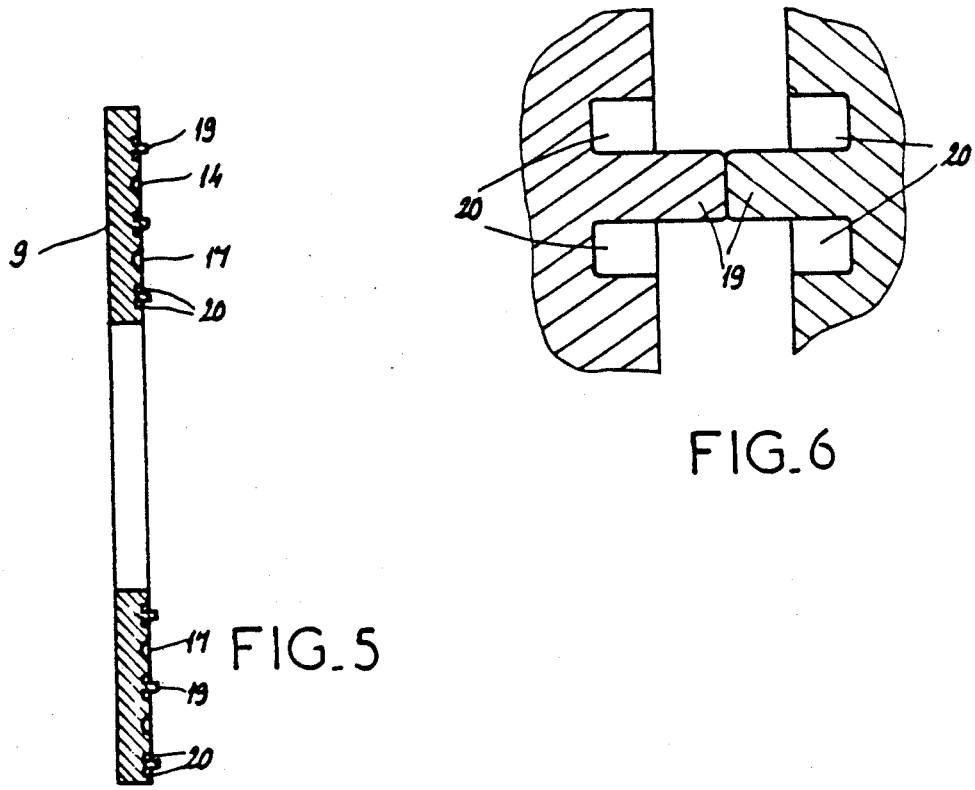
FIG.5
FIG.6

DEVICE FOR CLEANING AND DISINFECTING MEDICAL AND SURGICAL INSTRUMENTS

The object of the present invention is a device for cleaning and disinfecting medical and surgical instruments.

Practicians, whether surgeons, dental surgeons or doctors, use instruments which cannot always be sterilized or disinfected thoroughly between two successive operations. Such is notably the case for instruments which are dependent on the treatment console and which can be thoroughly cleaned only after protracted disassembly, and this cannot be achieved between two successive operations. For example, these instruments are manual components, counter-angle components, ultra-sound apparatus and three-way evaporators, all in constant use by dental surgeons.

Now, as these instruments can be subject to substantial staining from microbes or viruses contained in gangrenous teeth, dental plaque, in saliva or blood, it is important, as far as possible, to remove these stains in order to avoid risk of cross-contamination from one patient to another, or from a patient to medical personnel.

Such contamination has particularly serious consequences in the case of difficult-to-treat illnesses, such as hepatitis B, or illnesses for which no treatment is yet available, such as AIDS.

To rectify these drawbacks plans were made to produce a device comprising a tubular body, one end of which is open, allowing insertion of the instrument to be cleaned, the other end of which is fitted with a container for collecting liquid. The interior wall of the tubular body is provided with nozzles, arranged more or less radially, which, when instruments are placed in the hollow interior of the body, discharges an atomized disinfection product. On the one hand this product effects mechanical cleaning of the instruments, and on the other hand ensures disinfecting of the instruments, as any staining is directed to the collection container along with the atomized liquid, facilitated by the negative pressure created by an exhauster, while the condensation of the liquid cloud is facilitated by a system of baffle plates.

Nevertheless, known apparatus of this type does not give complete satisfaction on account of the inherent difficulties in effecting correct feed of the nozzles, notably of disinfectant liquid, especially if the liquid is not drawn off under pressure, but merely exhausted by the passage of air compressed by the nozzles. In effect, it is advisable to establish a system in which the drawn-off liquid is as balanced as possible, and which ensures firm sealing in the components housing the fluid distribution ducts.

The present invention aims to remedy the drawbacks of existing apparatus by providing a device in which the means of air supply and liquid supply of the various nozzles is kept simple, though still retains all the required features, notably in the area of equalization of the various nozzles.

To this effect the device for cleaning and disinfecting medical and surgical instruments concerned, of a type comprising a tubular body, one end of which is open and the other end of which opens into a collection container for waste liquid, and the interior wall of which is fitted with discharge nozzles for an atomized disinfection product, each nozzle being associated with an injector which attracts the disinfection liquid and the pressurized air, is characterized in that the means of air supply of the injectors comprise an annular and circular duct extending through 360°, arranged around the tubular body in a transverse plane to its axis, directly supplying the various injectors and also characterized in that the means of disinfection liquid supply comprise a first circular duct extending through 180°, arranged around the tubular body in a perpendicular plane to its axis, fed in its centre by the disinfectant liquid, and in the two ends of which two axial ducts open out, the other end of each of which opens into the centre of a circular duct extending through 90° in a transverse plane to the tubular body, while the two ends of each of these last ducts connect with an injector, or with a duct whose ends each supply an injector, according to the number of injectors making up the device itself.

Subdivision of the liquid supply duct into two ducts, which each subdivide into two supply ducts for the injectors, allows equalizing of the distances covered by the liquid between the source and each injector, in such a way that the load is the same for all injectors. If this feature is significant when the liquid is supplied under pressure, it is all the more so when the liquid is simply gravity fed and exhausted by pressurized air.

In this case where the device comprises four injectors the supply means for disinfection liquid comprise a first circular duct extending through 180°, arranged around the tubular body, in a perpendicular plane to its axis, fed in its centre by the disinfection liquid, and in the two ends of which two axial ducts open out, the other end of each of which opens into the centre of a circular duct extending through 90° in a transverse plane to the tubular body, while the two ends of each of these last ducts connect with an injector.

In accordance with an operational example of this device the supply means for air and disinfection liquid are formed by three juxtaposed crowns connected in pairs, in the surfaces opposite to which are channels designed to ensure the formation of circular ducts; the first crown comprises two axial bores for connection to the liquid and air supply ducts, the first and second crowns defining a first duct extending through an angle of 180° allowing the passage of liquid; the second crown comprises three axial bores, one for the direct passage of air and two for the passage of liquid, the second and third crowns defining on the one hand through 360° the circular duct for distribution of air to the injectors, and on the other hand through 90° defining each pair of ducts for distribution of liquid.

According to a feature of the invention the three crowns are made of synthetic material and their opposite surfaces comprise assembly means constituted by a plurality of circular flanges, opposite which each is edged by two grooves, each groove designed to form a duct arranged between two adjacent flanges of different diameter. This structure allows assembly of different crowns by the mirror welding technique. This feature is significant as it ensures simple and rapid assembly with excellent sealing, without use having to be made of either sealing joints or of locking joints.

The invention will be clearly understood with the assistance of the following description, with reference to the attached diagram representing by non-limiting example an operational example of this device:

FIG. 4 shows an exploded view of the three crowns comprising the device;

FIG. 5 shows a cross-section of one of the three crowns along the line V—V in FIG. 4;

FIG. 6 shows a sectional view of the detail of the assembly of two crowns.

Figure 1:
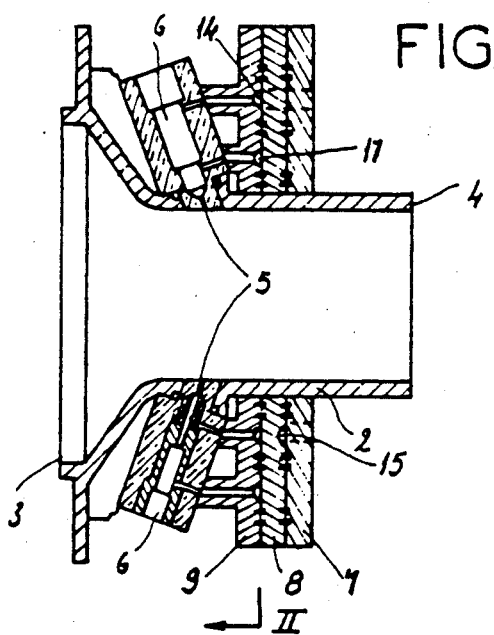
FIG. 1 shows a longitudinal section of the actual part to be cleaned.
Figure 2:
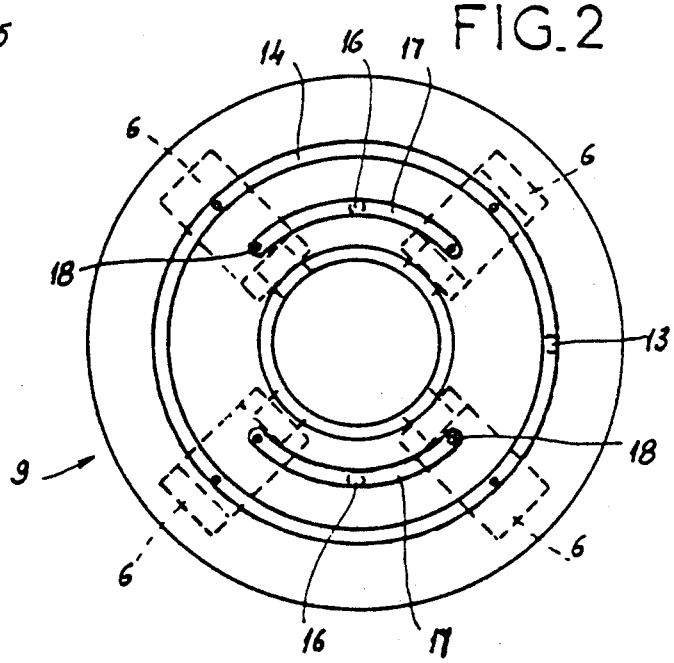
FIG. 2 shows a cross-section along the line II—II in FIG. 1.

The device according to the invention comprises a tubular body 2 the enlarged front end 3 of which allows insertion of an instrument for cleaning and the rear end 4 of which allows mounting of a collection container for liquid. Four nozzles 5 open into the interior wall of the tubular body off-set at 90° in relation to each other, each nozzle being fed by an injector 6 with a mixture of disinfection liquid and air to form a mist, the air being brought to each injector at a level outside the point of feed of the liquid. The means of feed for liquid and air to the injectors 6 are formed by three crowns 7,8,9 arranged outside the tubular body and connected in pairs to each other. The first crown 7 comprises two bores opposite which two coupling end-pieces 10 and 12 are connected to supply ducts for air and disinfectant liquid respectively. Opposite the end-piece and corresponding bore the crown 8 displays an axial bore 13 supplying air into an annular and circular duct 14 arranged in the crown 9 extending through 360°. The duct 14 feeds air to the four injectors 6.

Figure 3:
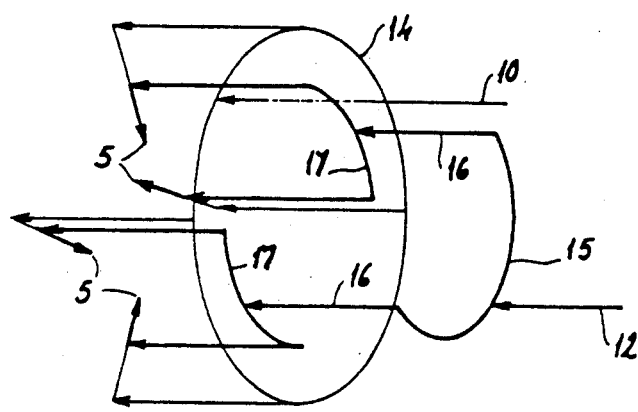
FIG. 3 shows a schematic view of distribution of air and disinfectant liquid for the injectors.

For its part, the end-piece 12 feeds, via the bore housed in the crown 7, a duct 15 housed in the crown 8. This duct 15 extends through 180°, that is 90° on either side of the position of the end-piece 12. At the ends of the duct 15 bores 16 are arranged, crossing the crown 8 and feeding in their centre two ducts 17, each extending through 90° and housed in the crown 9. At each end of a duct 17 a bore 18 is located which ensures supply of disinfectant liquid to an injector 6. The supply circuits of the injectors for air and liquid are depicted in FIG. 3. From the foregoing description it is clear that the liquid supply from the four injectors is effected in perfectly balanced fashion, in such a way that atomization is the same for all the injectors.

In order to ensure perfect sealing between the various crowns, without having to resort to joints or means of locking, the crowns have been assembled by a mirror welding technique.

To this effect, each crown comprises, as shown more especially in FIGS. 5 and 6, three circular assembly lines between which the ducts 14 and 17 are arranged, with regard to the assembly of the crowns 8 and 9. Each assembly line, on each surface opposite the two crowns, results from the presence of a material flange 19, on either side of which two grooves 20 are disposed. After supplying of the crowns at a temperature rendering the flanges malleable, the crowns are applied against each other under pressure; the associated movement is affected by joining of the flanges 19 with forward creep of residual material in the grooves 20.

As a result of the above the invention brings considerable improvement to the existing technique by providing a device for cleaning and disinfecting medical and surgical instruments of a straightforward design, in which the supply of liquid and air is effected in perfectly balanced fashion.

It stands to reason that the invention is not limited to a single operational example of this device described above by way of example; on the contrary, it encompasses all possible working variations. Thus it is notable that the number of injectors could vary or rather that the body of injectors could be perpendicular to the axis of the body of the device, the outlet of the injectors then being angled, without going beyond the scope of the invention.

The claims defining the invention are as follows:

1. A device for cleaning and disinfecting medical and surgical instruments, comprising:
    a tubular body, one end of which is open and the other end of which is open for passage of fluid into a collection container for waste liquid, the body having an interior wall and a longitudinal axis,
    a plurality of nozzles fitted on the interior wall for supplying atomized disinfection liquid within the tubular body,
    each said nozzle having an injector in fluid communication with the nozzle for supplying disinfection liquid and pressurized air to the nozzle,
    means for supplying pressurized air to the injectors comprising an annular first duct extending through 360° around the tubular body in a plane transverse to the longitudinal axis of the tubular body and means for providing fluid communication between the first duct and the injectors,
    means for supplying disinfection liquid to the injectors comprising an arcuate second duct extending 180° about the tubular body in a plane transverse to the longitudinal axis of the body, a fluid inlet located centrally of the ends of said second duct, a third duct comprising two arcuate sections, each section extending 90° about the longitudinal axis of the tubular body in a transverse plane spaced longitudinally from the plane of the second duct, means for providing fluid communication between each end of the second duct and a respective fluid inlet located centrally of the ends of each said section of the third duct; and means for providing fluid communication between each end of the two arcuate sections of the third duct and an associated one of the injectors.

2. A device as in claim 1, wherein the planes of the ducts are perpendicular to the longitudinal axis of the tubular body.

3. A device as in claim 2, wherein the means for supplying air and the means for supplying disinfection liquid comprise first, second and third juxtaposed crowns, the first and second crowns forming a first pair and the second and third crowns forming a second pair; and wherein the first, second, and third ducts are formed by the first and second pairs of said crowns.

4. A device as in claim 3, wherein the second duct is formed by the first pair of crowns and the third duct is formed by the second pair of crowns.

5. A device according to claim 3, wherein the three crowns are made of a synthetic material and wherein aligned circular flanges are located on opposing faces of the crowns to the crowns to each other.

6. A device as in claim 5, wherein a pair of annular grooves flanks each flange.

7. A device as in claim 3, wherein the second duct is formed by the first pair of crowns and the first duct and the third duct are formed by the second pair of crowns.

8. A device as in claim 7, wherein the first crown includes a first fluid inlet means for providing said disinfection liquid to the second duct and a second fluid inlet means for providing said pressurized air, and the second crown includes means for providing fluid communication between the second fluid inlet means and the first duct.

9. A device as in claim 8, wherein the first, second and third ducts are formed at least in part as recesses in surfaces of at least one of the crowns.

10. A device as in claim 9, wherein the three crowns are made of a synthetic material and wherein aligned circular flanges are located on opposing faces of the crowns to the crowns to each other.

11. A device as in claim 10, wherein each recess is flanked on either side by an opposed pair of said flanges.

12. A device as in claim 11, wherein a pair of annular grooves flanks each flange.

13. A device for cleaning and disinfecting medical and surgical instruments, comprising:
    a tubular body with an elongate longitudinal axis, the body having one end open for the insertion of instruments and the other end open for passage of fluid into a collection container, the body having an interior wall;
    a plurality of nozzles on the interior wall for supplying atomized disinfection liquid within the tubular body;
    each nozzle having an injector in fluid communication with the nozzle for providing disinfection liquid and pressurized gas to the nozzle;
    supply means for supplying said disinfection liquid and pressurized gas to the injectors, comprising:
    first, second and third annular crowns disposed about the body transversely of the longitudinal axis, the first and second crowns abutting to form a first pair of crowns and the second and third crowns abutting to form a second pair of crowns;
    a pressurized air duct formed by one of the pairs of crowns, the crowns including inlet means for providing pressurized gas to the duct and means for providing fluid communication between the duct and the injectors; and
    first and second disinfection liquid ducts, the first disinfection liquid duct formed by the first pair of crowns and the second disinfection liquid duct formed by the second pair of crowns;
    a disinfection liquid inlet means in the first pair of crowns for supplying disinfection liquid to the first disinfection liquid duct; means for providing fluid communication between the first disinfection liquid duct and the second disinfection liquid duct and means for providing fluid communication between the second disinfection liquid duct and the injectors.

14. A device as in claim 13, wherein the crowns are made of synthetic material and abutting surfaces of each pair of crowns include aligned flanges for welding the crowns together.

* * * * *